(12) United States Patent
Surai et al.

(10) Patent No.: US 6,235,783 B1
(45) Date of Patent: *May 22, 2001

(54) MALE FERTILITY WITH ANTIOXIDANTS AND/OR POLYUNSATURATED FATTY ACIDS

(75) Inventors: Peter Surai; Raymond Clifford Noble, both of Ayr (GB)

(73) Assignee: JSR Clover Ltd. (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,174

(22) PCT Filed: Jun. 30, 1997

(86) PCT No.: PCT/GB97/01735

§ 371 Date: Feb. 24, 1999

§ 102(e) Date: Feb. 24, 1999

(87) PCT Pub. No.: WO98/00125

PCT Pub. Date: Jan. 8, 1998

(30) Foreign Application Priority Data

Jun. 29, 1996 (GB) .................................................. 9613754
Feb. 26, 1997 (GB) .................................................. 9704018

(51) Int. Cl.[7] ........................ A61K 31/20; A61K 31/355
(52) U.S. Cl. ......................... 514/560; 514/558; 514/458
(58) Field of Search .................................. 514/558, 560, 514/458

(56) References Cited

FOREIGN PATENT DOCUMENTS

97/16965    5/1997   (WO) .

OTHER PUBLICATIONS

H.M.Sinclair, "Essential Fatty Acids in Perspective", Human Nutrition: Clinical Nutrition, vol. 38, No. 4, 1984, pp. 245–260.

Paulenz et al., "A Preliminary Study on the Effect of Dietary Supplementation with Cod Liver Oil . . . ", Veterinary Research Communications, vol. 19, No. 4, 1995, pp. 273–284.

Kessopoulou et al., "A double–blind randomized placebo cross–over controlled trial using the antioxidant vitamin E . . . ", Fertility and Sterility, vol. 64, No. 5, 1995, pp. 825–831.

Geva et al., "The effect of antioxidant treatment on human spermatoza and fertilization rate in an in vitro fertilization program", Fertility and Sterility, vol. 66, No. 3, 1996, pp. 430–434.

Sharma et al., "Role of Reactive Oxygen Species in Male Infertility", Urology, vol. 48, No. 6, 1996, pp. 835–850.

Aurich et al., "Effects of Antioxidants on Motility and Membrane Integrity of Chilled–Stored Stallion Semen", Theriogenology, vol. 48, No. 2, 1997, pp. 185–192.

*Primary Examiner*—Russell Travers
*Assistant Examiner*—Shengjun Wang
(74) *Attorney, Agent, or Firm*—Heslin & Rothenberg, P.C.

(57) ABSTRACT

A method of controlling the viability of sperm is disclosed, the method comprising controlling the levels of antioxidants (and/or polyunsaturated fatty acids) in sperm or seminal fluid, or in the diet of the animal producing the sperm.

9 Claims, 12 Drawing Sheets

MALE FERTILITY WITH ANTIOXIDANTS AND/OR POLYUNSATURATED FATTY ACIDS

This application is the U.S. national phase application of PCT International Application No. PCT/GB97/01735 filed Jun. 30, 1997.

This invention relates to improvement of male fertility.

All animal species' spermatozoa have high concentrations of polyunsaturated phospholipids. In mammalian species e.g. the bull, boar, ram and man, the substantial level of polyunsaturates present is characteristically dominated by docosahexaenoic acid (22:6, n-3), a fatty acid of 22 carbon atoms in chain length, containing 6 double bonds in n-3 conformation and belonging to the alpha-linolenic acid (18:3, n-3) series. Thus in the case of the bovine, docosahexaenoic acid accounts for around 55% of the total phospholipid fatty acids, with particular concentrations occurring within the phosphatidyl ethanolamine and phosphatidyl choline species. By contrast, avian spermatozoa exhibit in general very low concentrations of docosahexaenoic acid and acids of the n-3 series but this is compensated for by the presence of substantial concentrations within the phospholipids of polyunsaturated fatty acids having chain lengths of 20 and 22 carbon atoms, containing 4 double bonds in n-6 conformation and belonging to the linoleic acid (18:2, n-6) series; these are arachidonic (20:4, n-6) and docosatetraenoic acid (22:4, n-6) respectively.

The lipid composition of the spermatozoan membrane may be a major determinant of motility, cold sensitivity and a wide selection of factors associated with overall viability within fresh ejaculates or stored ejaculates maintained at −196° C. for artificial insemination.

According to the present invention there is provided an antioxidant to enhance sperm function and/or viability.

Further according to the present invention there is provided a polyunsaturated fatty acid (PUFA) to enhance sperm function and/or viability.

Still further according to the present invention there is provided an antioxidant accompanied by a PUFA to enhance sperm function and/or viability.

The antioxidant and/or PUFA may be administered to the animal producing the sperm, for example in its diet, or intravenously or intramuscularly, or may be added to the sperm or to fluid surrounding the sperm.

Preferably the antioxidant is selected from vitamins, plant extracts and carotenoids.

Preferably the PUFA is an n-3 fatty acid, for example docosahexaenoic acid (DHA) or another member of the alpha-linolenic acid (18:3, n-3) series.

In a further aspect, the present invention provides a method of enhancing sperm function and/or viability, comprising adding to the semen of an animal substantially sperm-free seminal fluid containing an antioxidant and/or a PUFA.

The seminal fluid is preferably produced from the semen of another animal which may have been vasectomised or from whose semen sperm has been removed.

The mixture of the semen and seminal fluid can then be stored at low temperature for use in artificial insemination.

The semen in this aspect of the invention may already have been boosted in function or viability by virtue of the animal having antioxidant and/or PUFA administered to it. The PUFA is preferably administered to the animal in an amount of at least 10 mg/kg of body weight, most preferably 10–45 mg/kg.

The invention also provides a method of enhancing the function and/or viability of sperm, the method comprising controlling the PUFA content of the sperm, preferably the plasma membrane of the sperm, although the control of PUFA content of the seminal plasma can also be of benefit. The PUFA content of the plasma membrane can be controlled eg by adding PUFA or antioxidant to the sperm directly or administering the PUFA or the antioxidant to the animal's diet.

The invention also provides a method of combatting sperm dysfunction, comprising controlling the PUFA content of the sperm, preferably the content of the sperm plasma membrane, eg by exposing the sperm to a PUFA or an antioxidant.

The term "combat" as used herein refers to the prevention of a condition (ie prophylactic use) as well as treatment of an existing condition to ameliorate that condition or to delay or prevent its further deterioration.

The PUFA can be added direct to the ejaculate, or can be administered to an animal to enhance the function and/or viability of sperm from that animal. In such a case, the PUFA is preferably administered in quantities of at least 10–45 mg/kg body weight. The PUFA can be provided in substantially pure form or in combination with a pharmaceutical carrier or excipient, or in impure form. For example, the PUFA may be provided in the form of fish oil, or can be extracted from brain tissue by conventional methods. The PUFA may be incorporated into the fatty acid pool of the sperm, or may remain in the seminal fluid in order to exert its beneficial effects.

The PUFA is preferably a C18–C24 fatty acid.

The viability can be enhanced by increased mobility, cold resistance or related factors.

Two embodiments of the invention include:

(i) the maximisation of male fertility in vivo through the dietary manipulation of the lipid composition and/or antioxidant capacities of the fresh ejaculate.

(ii) the development of effective antioxidant/lipid additives for semen diluents and effective carrier systems for inclusion of the additives into the sperm membrane in order to ensure sperm viability in vitro and in vivo and fertility capacities after storage.

MATERIALS AND METHODS

Figure 1:
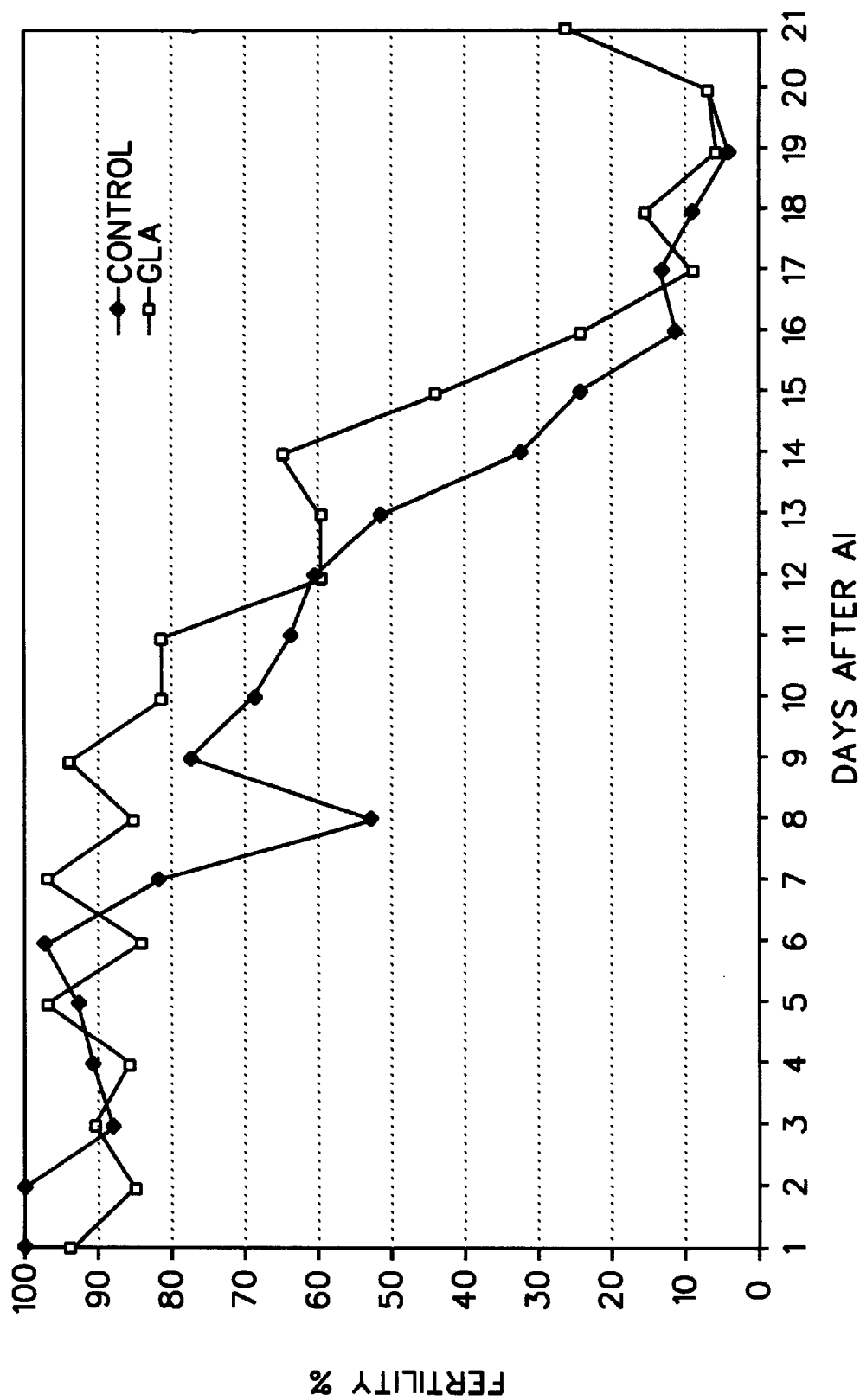
FIG. 1 is a graph of fertility rate on a daily basis after a single artificial insemination with a fixed dose of $10 \times 10^7$ spermatozoa.

The investigations involved both avian (cockerel) and mammalian (bull) species.

(i) Avian dietary treatments.

(a) Supplementation with alpha-linolenic acid (18:3 n-3).

Two groups, each of 15 male broiler breeders from the same genetic stock, were purchased from a commercial breeder supplier. The males were 21 weeks of age at the beginning of the experiment and 72 weeks old at the end. The males were housed in single cages in a controlled environment with a photoperiod of 13 hours light: 11 hours dark. They were each fed 130 g per day of feed with 12.5% crude protein and 11.5 MJ/kg of ME. The control diet was supplemented with soyabean oil (6% w/w of feed) and the 18:3 (n-3) enriched diet was produced by supplementation with linseed oil (6% w/w of feed), see Table 1. Regular lipid analysis of feed was undertaken to establish the lipid and fatty acid composition. The males were trained for semen collection from 21 weeks of age and were milked routinely twice weekly throughout the experimental period and three times on the weeks 24, 40 and 54 chosen for laboratory analysis. Lipid analysis was performed on 5 pooled semen samples.

(b) Dietary supplementation with docosahexaenoic acid (22:6 n-3).

Two groups, each of 12 male broiler breeders from the same genetic stock were used. The males were 11 weeks of age at the beginning of the experiment with semen being collected at 24 weeks and 38 weeks of age. Housing, treatment and control diet were as per example 1. The 22:6 (n-3) enriched diet was produced by supplementation with a 22:6 (n-3) enriched fish oil extract (3% w/w of feed), see Table 1. Semen collection was as described in (i)(a).

A second trial involving dietary supplementation with 22:6 (n-3) was subsequently undertaken. Details of the diet, housing and general management of the cockerels were as for the first trial. The 22:6 (n-3) was delivered by the inclusion in the diet of the fish oil at a rate of 5% w/w within the feed. Semen collection was performed as per (i)(a) above with investigations of chemical and physiological parameters being undertaken on samples at 24, 40 and 58 weeks of age. In this experiment there was a further experimental group in which 22:6 (n-3) was accompanied by the inclusion of 200 mg/kg of α-tocopherol in the diet.

(c) Supplementation with gamma-linolenic acid (18:3.n-6).

Two groups, each of 20 male broiler breeders from the same genetic stock were used. The males were 21 weeks of age at the beginning of the experiment. Housing, treatment and control diet were as per (i)(a) above. The $^1$8:3(n-6) enriched diet was produced by supplementation with evening primrose oil (5% w/w of feed) containing 9% w/w of 18:3 (n-6), see Table 1. Semen was collected five times a week at 40 weeks of age. Lipid analyses was performed on 7 individual samples.

(ii) Bull dietary treatments

Two groups, each of three Holstein/Freisian bulls from Scottish Livestock Services AI Centre, Perth, Scotland comprised the main locus of experimentation; in addition, observations were made on a Belgian Blue bull, a breed known for its inherently low level of male fertility. Each bull was kept under standard (and conventional) conditions appropriate to a leading AI centre. All the bulls were fed twice daily 3 kg of a standard diet delivering 12.5 MJ/kg ME and 15% crude protein. Following appropriate collection and sampling of the ejaculates, each bull was then switched to a diet, based on the standard diet, but which for each 3 kg delivered 90 g of a fish oil containing 25% 22:6 (n-3). Thus with the average bull weighing 800 kg, delivery of 22:6 (n-3) was some 45 mg per kg body weight. The bulls were then sampled after an 8 week period on this diet. The major fatty acid within the diets are shown in Table 1. Semen was collected by artificial vagina.

(iii) Spermatozoa evaluation.

In the case of the cockerels sperm quality measurements were made at 24, 39 and 54 weeks of age. Pooled semen samples of 3 ejaculates (5 replicates per group) were analysed in each case. In the case of the bulls, semen was collected every 2 weeks over the complete period of the experiment. Within 20 minutes of collection appropriate semen parameters were measured that included ejaculate volume, sperm concentration, acrosomal integrity and motility using microscopic and Cellsoft Computer Assisted Analysis. Fertility in the cockerels was assessed by insemination of laying hens with a fixed dose of semen ($70 \times 10^6$ cells/ml). Eggs were collected for 2 weeks for groups (i)(a) and (i)(b) and 3 weeks for (i)(c) and incubated for 7 days before candling to record the presence of any embryo. Weekly fertilities were measured in groups (i)(a) and (i)(b) and daily for (i)(c).

(iv) Preparation of semen for lipid extraction.

Semen was diluted with an equal volume of 0.85% (w/v) sodium chloride solution and centrifuged at 700 g for 20 minutes at 4° C. The upper diluted plasma layer was transferred to a fresh tube, the wash procedure was repeated with 1 ml of 0.85% (w/v) sodium chloride and the final cell pellet was re-suspended in 2 ml of 0.85% (w/v) sodium chloride. In order to obtain sufficient material for analysis from each individual cockerel, the successive samples obtained during the 3 week collection period were combined.

(v) Lipid analysis.

Total lipids were extracted from the spermatozoa preparations following homogenisation in a suitable excess of chloroform:methanol (2:1 v/v). The lipids were fractionated into their major classes (phospholipid, free cholesterol, triacylglycerol, free fatty acids and cholesterol ester) by thin layer chromatography on silica gel G using a solvent system of hexane:diethyl ether:formic acid (80:20:1 v/v/v). Following visualisation under UV light after spraying with 0.1% w/v solution of 2,7-dichlorofluorescein in methanol, the separated bands were scraped from the plates. Phospholipid was eluted from the silica by washing 3 times with 2 ml methanol and the other lipid classes were similarly eluted with diethyl ether. The esterified lipid fractions were subjected to transmethylation by refluxing with methanol:toluene:sulphuric acid (20:10:1 v/v/v) in the presence of a pentadecanoic acid standard. The resultant fatty acid methyl esters were analysed by 1 µl injection, via a CP9010 auto sampler (Chrompack, London, UK), on to a 30 m×0.25 mm diameter, 0.25 µm film thickness Carbowax capillary column (Alltech UK Ltd., Carnforth) fitted to a Chrompack CP9001 instrument (Chrompack, London, UK). Integration of the peaks using an 'EZ-Chromr' Data Handling System (Speck Analytical, Alloa, UK) enabled the derivation of the fatty acid composition (% w/w of total fatty acids). The amount of each lipid class was calculated by comparison of the total fatty acid peak areas to that of the pentadecanoic fatty acid standard. Free cholesterol was determined by standard calorimetric assay (Boehringer, Lewes, UK). Individual phospholipid classes were separated by high performance thin layer chromatography (HPTLC) using a solvent system of methyl acetate: isopropanol:chloroform:methanol:0.25% (w/v in $H_2O$) KCl (25:25:25:10:9 v/v/v/v/v). After charring, quantification was performed by densitometry using a Shimadzu CS-9001 PC dual wavelength flying spot thin layer scanner (Shimadzu Corporation, Japan).

(vi) Statistical Analysis.

Students t-test was used for all statistical comparison. Data included 5+4 replicates respectively for the cockerels and bulls included 5 replicates per group at each collection period for lipid analysis and 15 and 8 replicates per group at each collection period for semen evaluation. For cockerels in groups (i)(a) and (i)(b) 5 replicates within each week of egg collection at each collection period were used for assessment of fertility and for cockerels in group (i)(c) 7 replicates were used for assessment of fertility.

(vii) Bull semen diluent

Bulls of known reproductive performance were selected from Holstein/Fresian and Belgian Blue breeds. Both groups were known to exhibit problems with routine freezing of their semen, particularly with respect to post-freeze survival of spermatozoa and maintenance of acrosomal integrity. The bulls were 5–6 years of age and housed/fed according to accepted commercial AI practice.

α-tocopherol additives for addition to fresh diluted ejaculates were as follows: treatment A, (control) no α-tocopherol, no semen diluent; treatment B. 10 mg/ml α-tocopherol, skimmed milk diluent; treatment C, 1 mg/ml α-tocopherol, skimmed milk diluent; treatment D, 10 mg/ml α-tocopherol, egg yolk/biosophus plus diluent; treatment E, 1 mg/ml α-tocopherol, egg yolk/biosophus plus diluent; treatment F, 10 mg/ml α-tocopherol, egg yolk/0.85% (w/v) saline diluent; treatment G, 1 mg/ml, egg yolk/0.85% (w/v) saline diluent.

Additive preparation: α-tocopherol in milk buffer.

To prepare the diluent, 5–50 mg of DL-α-tocopherol was carefully weighed into a fresh test tube. Immediately afterwards 5 ml of fresh skimmed milk buffer was added and the preparation mixed thoroughly. To disperse and ensure complete solubilisation of the vitamin in the milk the preparation was homogenised thoroughly for 30–40 seconds followed by 10–15 seconds of sonication until a clean, milky texture was obtained. The contents of the test tube were then carefully poured into a darkened glass vial, plugged and stoppered. The vial was stored immediately at 4° C. and out of any direct sunlight to keep the vitamin and milk in the best condition for addition to the semen.

α-tocopherol in egg yolk.

Fresh egg yolk was used to aid in solubilisation of the lipid-soluble α-tocopherol. A stock solution of Biosophus Plus 1:4 (v/v) in distilled water was prepared and mixed thoroughly by manual inversion. A few drops of egg yolk were placed in the bottom of a clean test-tube and 5–50 mg of α-tocopherol were carefully weighed with the drops being placed directly onto the egg yolk. The resultant mixture was then diluted with 5.0 ml of the Biosophus Plus solution and homogenised and stored as described above.

α-tocopherol in saline buffer.

This was prepared as described above using 5.0 ml of physiological saline (0.85% sodium chloride w/v).

In all cases the uniformity of distribution of the =60 - tocopherol throughout the diluent was confirmed before use by sub-sampling and appropriate analysis based on high performance liquid chromatography.

Semen dilutions.

Fresh semen from each bull was placed in a water bath at 37° C. and treated as per routine semen preparation procedures according to commercial AI practice. Each ejaculate was divided equally into the required aliquots for the addition of the additives. 100 ul of each additive was added to 1 ml of fresh semen. Semen straws were prepared containing 200 ul of semen plus diluent with a concentration of $2.5 \times 10^7$ spermatozoa per straw. For each treatment 10 straws were prepared, half being used for in vitro pre-freeze determinations and the remainder stored at −196° C. for post-freeze determinations 7 days later.

Results were obtained from 4 separate collection periods per bull. Artificial insemination and assessments of in vivo fertility procedures were performed according to standard AI practices. All analytical procedures were undertaken as per standard methodologies.

(viii) Avian semen diluent.

In the case of the avian a single carrier for the α-tocopherol in the semen diluent was assessed. It was based on the use of seminal plasma harvested from ejaculates of donor birds of the same breed/stock on which the tests were to be made. The seminal plasma was harvested by appropriate centrifugation of fresh semen and in particular, extreme care was taken to ensure the complete absence of any contaminating cells.

To 10 mg of α-tocopherol in an appropriate clean glass tube was added 5–10 ml of the seminal plasma. The whole was then homogenised for 3–5 minutes followed by sonication for 1–2 minutes to ensure thorough mixing. From this stock solution, varying amounts were added to diluted fresh semen to give a final concentration of between 10–500 ug α-tocopherol per ml of semen. The semen was then exposed to combinations of a selection of storage conditions embracing temperatures of 4° and 37° C. and times of 6, 12, 24, 48 and 72 hours. Following exposure the ejaculates were evaluated for in vivo fertility and in vitro assessment e.g. live sperm numbers, motility, chemical parameters by standard microscopic and analytical procedures but to include also specific tests of sperm viability based on measurements of membrane integrity by ethidium bromide and respiration using tetrazolium (reductase activity). A further test of sperm viability promotion was undertaken involving the comparison of these measurements in the presence or absence of $Fe^{++}$ as a stimulus for oxidation.

Statistical Analysis

Students t-test was used for all statistical comparisons. Analysis of variance and correlations were undertaken as appropriate.

Results

Dietary Supplementation (i) Cockerel (a) Supplementation with alpha-linolenic acid (18:3 n-3).

The effects of dietary supplementation with 18:3 (n-3) on the characteristics of the semen samples obtained from cockerels at 24, 40 and 54 weeks of age are shown in Table 2. For the cockerels on the control diet, the concentration of spermatozoa in the semen increased considerably between 24 and 40 weeks of age and then decreased markedly to 54 weeks. Dietary supplementation with 18:3 (n-3) significantly increased spermatozoa concentration at 54 weeks. Also, at 54 weeks the spermatozoa motility was significantly increased by the supplementation. In the control cockerels, fertility increased to a maximum at 40 weeks but had decreased by 54 weeks. The n-3 supplementation resulted in a significant increase in week 1 fertility at 40 weeks. Although fertility was not enhanced at 54 weeks, observations of the fertility at 72 weeks (not shown) were enhanced by n-3 supplementation.

The proportions of the major lipid and phospholipid classes of the spermatozoa are given in Table 3. The concentration of the total lipid in the spermatozoan cells increased continually with age; although not significant these values were higher for the supplemented birds at 40 and 54 weeks. Phospholipid was the major lipid class at all stages. However, the proportion of phospholipid decreased considerably with age. Supplementation with 18:3 (n-3) did not result in any dramatic effects on the proportions of the major lipid classes. Phosphatidyl choline and phosphatidyl ethanolamine were the main classes of phospholipid but there were no major effects of n-3 supplementation on the proportions of the major phospholipid classes.

The polyunsaturated fatty acid compositions of the total spermatozoan phospholipid from control and n-3 supplemented cockerels are presented in Table 4. The major polyunsaturated fatty acids in the control samples were 20:4 (n-6) and 22:4 (n-6); the phospholipids were almost devoid of n-3 polyunsaturates apart from the presence of very low levels (approximately 2% w/w) of 22:6 (n-3). Dietary supplementation with 18:3 (n-3) resulted in small but significant effects on these fatty acid profiles. Thus n-3 supplementation increased the levels of 22:5 (n-3) at 40 and 54 weeks and 22:6 (n-3) at 54 weeks. Whereas the levels of 22:6 (n-3) within the phosphatidyl ethanolamine fraction, normally the major carrier of the acid, in the control samples at weeks 40 and 54 were negligible, within the treated birds the levels were 2.2 and 3.1% respectively of total fatty acids present. However, most notably supplementation resulted in considerable decreases in the C20–22 n-6:n-3 ratios at weeks 40 and 54.

(b) Supplementation with docosahexaenoic acid (22:6 n-3).

Supplementation of the cockerels with 22:6 (n-3) resulted in an intensive change in overall appearance and visual parameters of assessment of the ejaculates at 40 and 58 weeks of age. Sperm concentration displayed a rise from $2.08 \times 10^9$/ml for the control group to 2.23 and $2.40 \times 10^9$/ml at 40 and 58 weeks of age respectively for the treated group. A significant increase in fertility as measured by AI was observed, 40.5±6.6(SE), 55.4±4.2 and 68.5±4.9 respectively. As can be seen in Tables 5 and 6 the levels of 22:6 (n-3) within the total phospholipid of the sperm and throughout all the major individual phospholipid moieties underwent a significant increase to accompany this increase in fertility. At the same time there were extensive and appropriate reductions in total n-6:n-3 fatty acid ratios. At slaughter at 60 weeks of age testis (single) weight in the control group was 15.1 g±1.4 compared with 22.3 g±3.0 for the cockerels supplemented with 22:6 (n-3) with no change in body weights.

In the second experiment involving 22:6 (n-3) supplementation, the compositional changes within the sperm were similar in both absolute and relative terms to those described for the first experiment (see Tables 5 and 6). Although the inclusion of α-tocopherol did not enhance to any significant degree the levels of polyunsaturates, the content of α-tocopherol in the spermatozoa was significantly increased by 60–70% above the other groups. Inherently the birds used in this experiment were more fertile (increased sperm number per unit volume of ejaculate etc.) than for the first experiments. Again supplementation of the cockerels with 22:6 (n-3) resulted in extensive changes in overall appearance and visual parameters of assessment of the ejaculates at 40 and 58 weeks of age. Spermatozoa concentration and other major parameters of fertility are shown in Table 7. As can be seen, semen volume, total spermatozoa number and fresh and stored fertilities were all significantly enhanced; relative spermatozoa motilities were increased by some 15% The inclusion of α-tocopherol had an added effect on fertility after storage. Testis weights (weights of 2 testes per bird) were again significantly increased by 22:6 (n-3) treatment without any accompanying differences in body weight. Investigations on the distribution of 22:6 (n-3) within the spermatozoan cell showed a preferential incorporation of the acid into the mitochondria. An important feature arising from the dietary enhancement with 22:6 (n-3) was an improved fertility of eggs during the 2nd week after artificial insemination. In approximate terms this equated with an extra 1.7 eggs becoming available over the whole 2 week period of the fertility investigation compared to the control treatments.

Supplementation with gamma linolenic acid (18:3 n-6)

Fatty acid compositions of the major lipid fractions were unchanged as a result of supplementation with 18:3 n-6. Major spermatozoa features associated with increased fertility were significantly increased by 18:3 n-6 supplementation (see Table 8); these embraced motility and fertilities over 1st, 2nd and 3rd weeks after artificial insemination. FIG. 1 shows the fertility rate on a daily basis following a single insemination of a fixed dose of $10 \times 10^7$ spermatozoa. As can be seen a positive difference in fertilities was prominent over the 2nd week in particular but also over the initial part of the 3rd week following insemination by the 18:3 (n-6) group compared to the control. This difference equated to an extra 2 fertile eggs per hen over the 2nd week following artificial insemination.

(ii) Bull

As can be seen from a comparison of the various parameters of sperm evaluation on the 2 diets (see Table 9), the switch to the diet to which had been added 22:6 (n-3) had a significant effect across the board on sperm fertility characteristics. Appropriately the levels of 22:6 (n-3) within the phosphatidyl ethanolamine fraction, that is the major phospholipid moiety associated with 22:6 (n-3), underwent a significant increase from a pre treatment level of 33.3±1.0 (S.E.) to 60.6±0.7(S.E.) following treatment (p<0.001). Due to commercial considerations, appropriate fatty acid analysis on the ejaculate of the single Belgian Blue bull was not possible.

Semen Diluents (i) Bull

Determination of α-tocopherol concentrations within the semen routinely showed that samples from group A (control) displayed low levels only of α-tocopherol, the levels increasing by some 100 fold with 1 mg/ml α-tocopherol supplementation and 1000 fold with 10 mg/ml α-tocopherol supplementation. Highest levels of malondialdehyde within the semen following storage at −196° C. were associated with group A and lowest levels with 10 mg/ml α-tocopherol supplementation. In vitro parameters of semen quality prior to freezing for the 2 groups of bulls are shown in Tables 10 and 11. The protocol for commercial semen sale requires a minimum of 3.5 and 35% for motility and PPM values respectively for both fresh and frozen semen analysis. Semen failing to meet such requirements would be discarded. As can be seen, semen from Group A (control) exhibited values approximately equal to these minima. By comparison 3 of the treatments showed a selection of improvements in motility and greater survival characteristics. In vitro parameters of semen quality post freezing at −196° C. for the 2 groups of bulls are shown in Tables 12 and 13. Although the quality of the Belgian Blue semen was not acceptable for commercial use, improvements were evident as a result of treatment. Marked improvements in parameters were exhibited by the Holstein/Fresian bulls.

Table 14 gives the results from insemination using Group B semen samples from the Belgian Blue bulls following storage at −196° C. As can be seen, in field experiments the treated semen resulted in a considerable enhancement of pregnancy.

Cockerel

Figure 2:
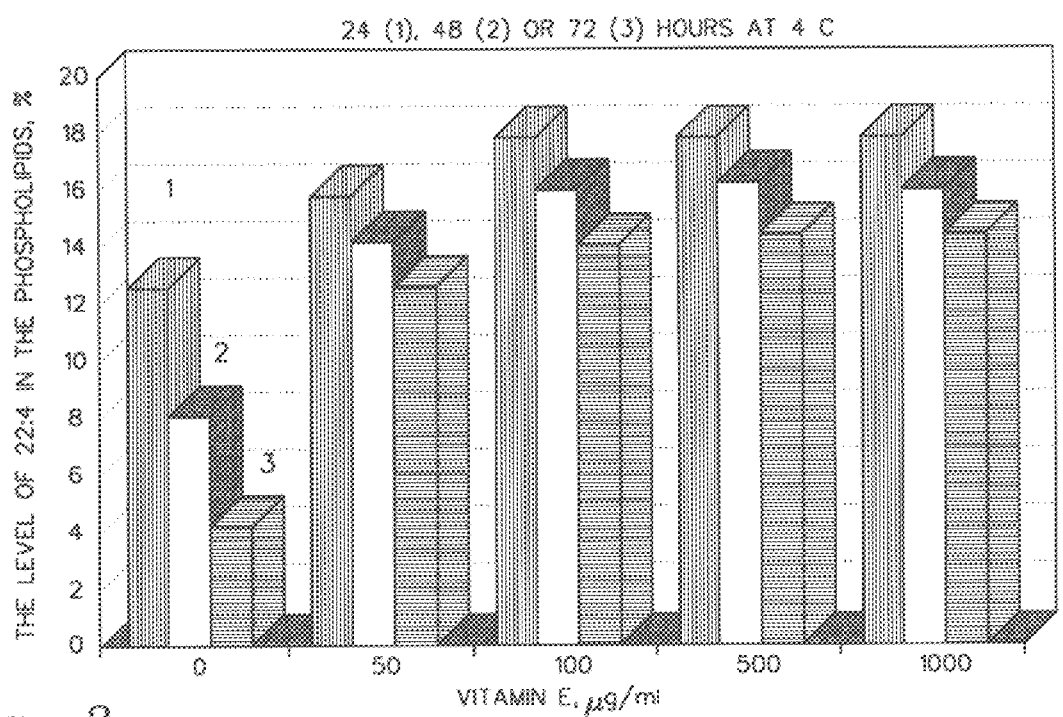
FIG. 2 is a graph depicting the levels of 22:4 fatty acid in sperm phospholipids vs vitamin E added after storage during 24 (1), 48(2) or 72 (3) hours at 4° C.
Figure 3:
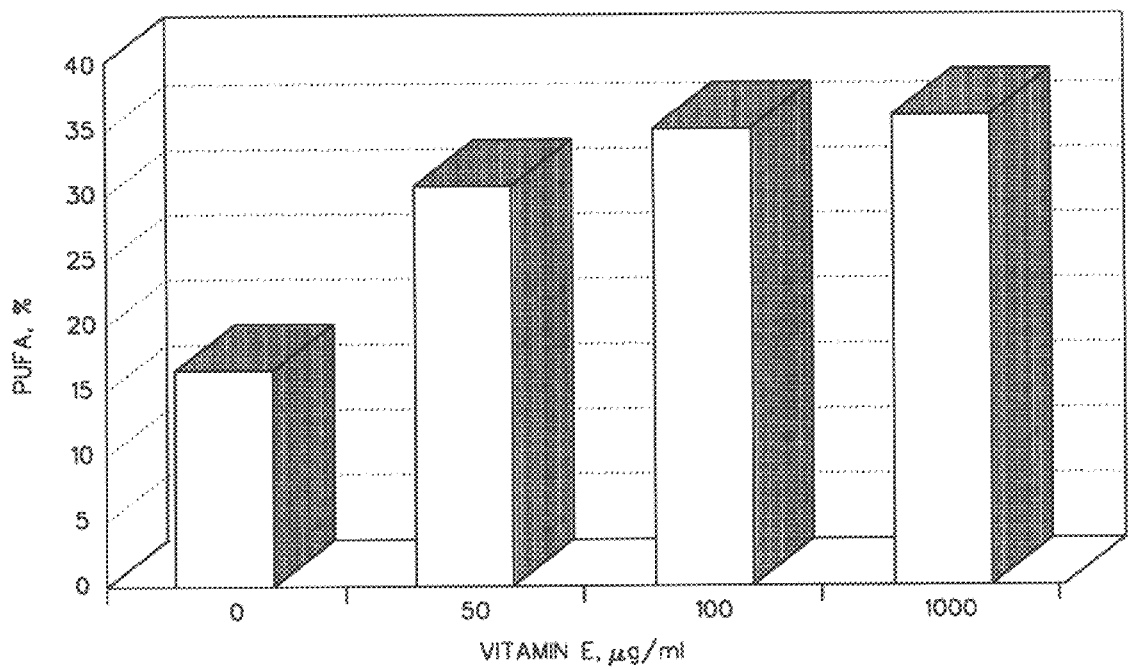
FIG. 3 is a graph depic levels of polyunsaturated fatty acids in sperm phospholipids vs vitamin E added.

The inclusion of α-tocopherol into the diluent, using harvested seminal plasma as a carrier, significantly increased resistance of the spermatozoa lipids to oxidation as based on an extensive range of biochemical parameters. Thus the level of 22:4, the most susceptible fatty acid to the lipid oxidation, in the spermatozoa phospholipids after storage was significantly higher compared to the control spermatozoa without vitamin E supplementation (see FIG. 2). The stabilising effect was seen during the full 24–72 hours of the spermatozoa storage at 4° C. The increase in storage temperature caused a pronounced reduction in the level of the long chain polyunsaturated fatty acids in the phospholipids. Under such conditions the diluent was also effective as a protective agent against oxidation (see FIG. 3).

Figure 4:
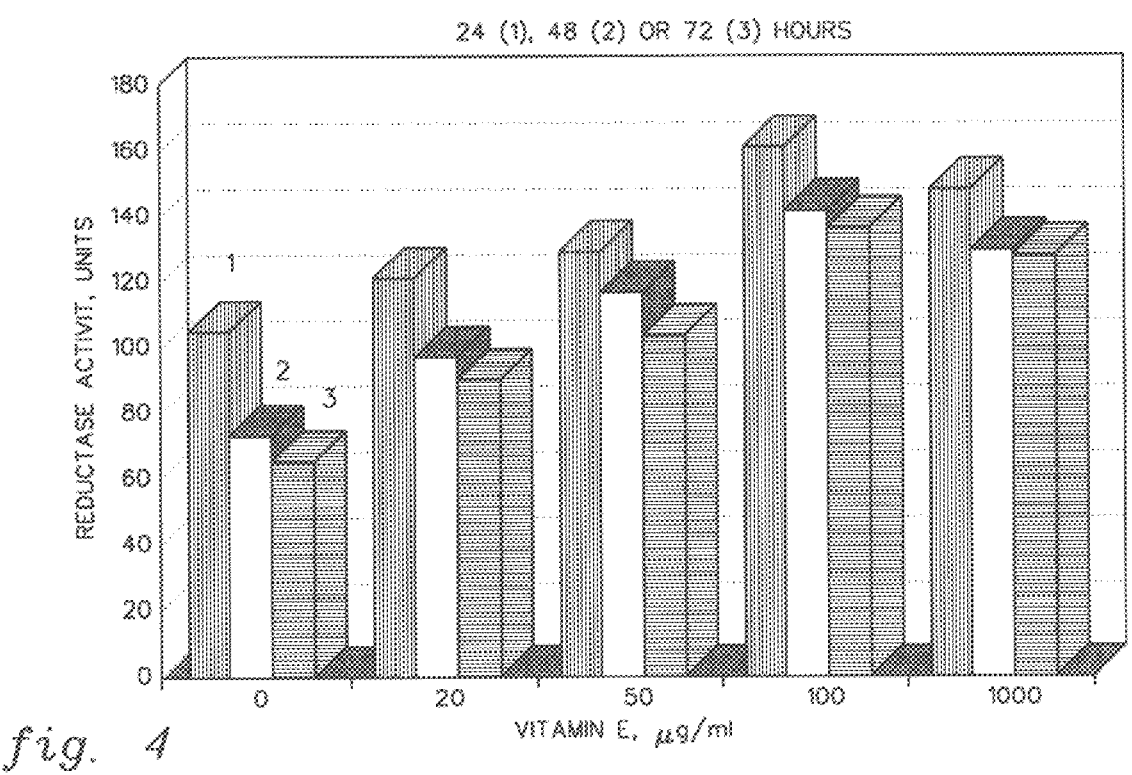
FIG. 4 is a graph depicting reductase activity in sperm vs vitamin E added after storage during 24 (1), 48(2) or 72 (3) hours at 4° C.
Figure 5:
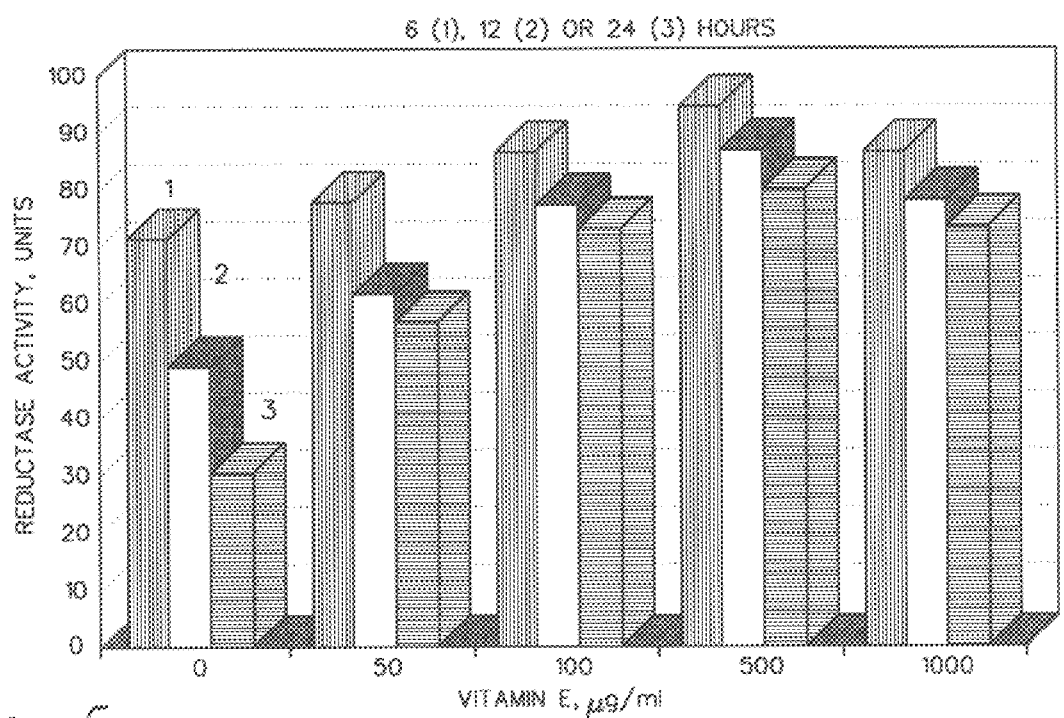
FIG. 5 is a graph depicting the levels of reductase activity in sperm vs vitamin E added after storage during 6 (1), 12(2) or 24 (3) hours at 37° C.

Storage was also associated with reduction of reductase activity, a feature that reflects damage to the respiratory chain of mitochondria of the spermatozoa involving peroxidation of the mitochondria lipids. The diluent clearly preserved the spermatozoa mitochondria lipids from oxidation and promoted reductase activity at both 4° C. and 37° C. (see FIGS. 4 and 5 respectively).

Figure 6:
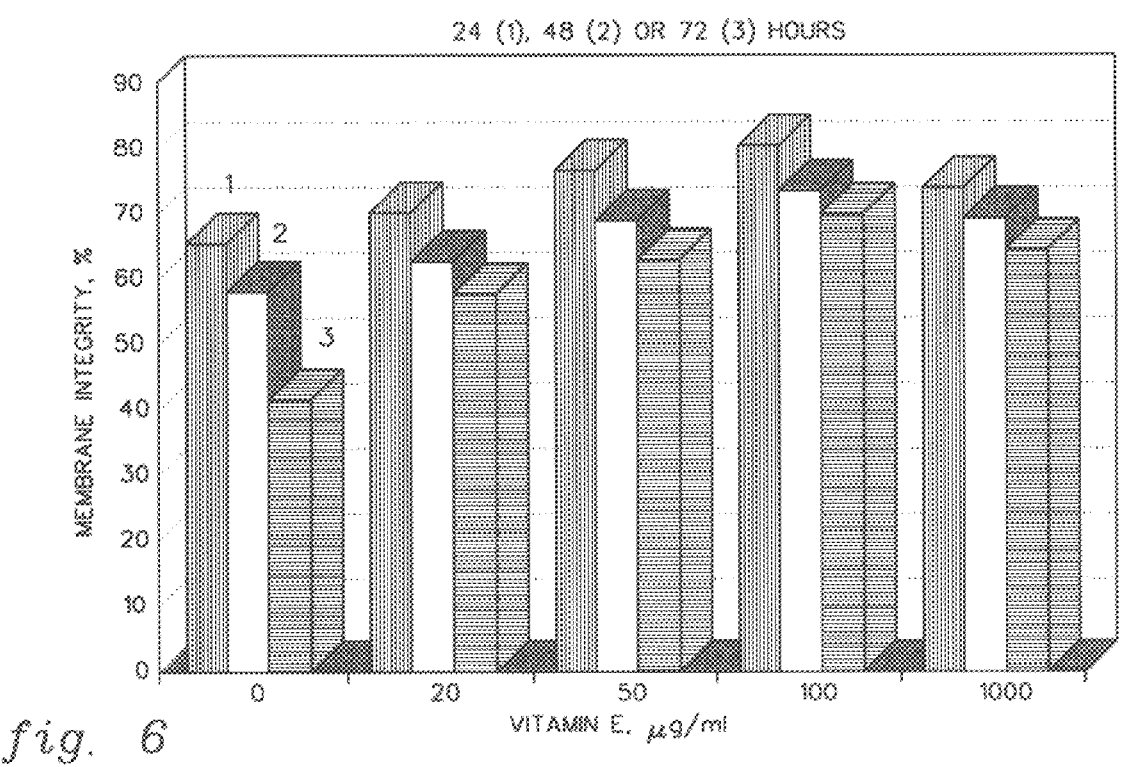
FIG. 6 is a graph depicting sperm viability vs vitamin E added after storage during 24 (1), 48(2) or 72 (3) hours at 4° C.
Figure 7:
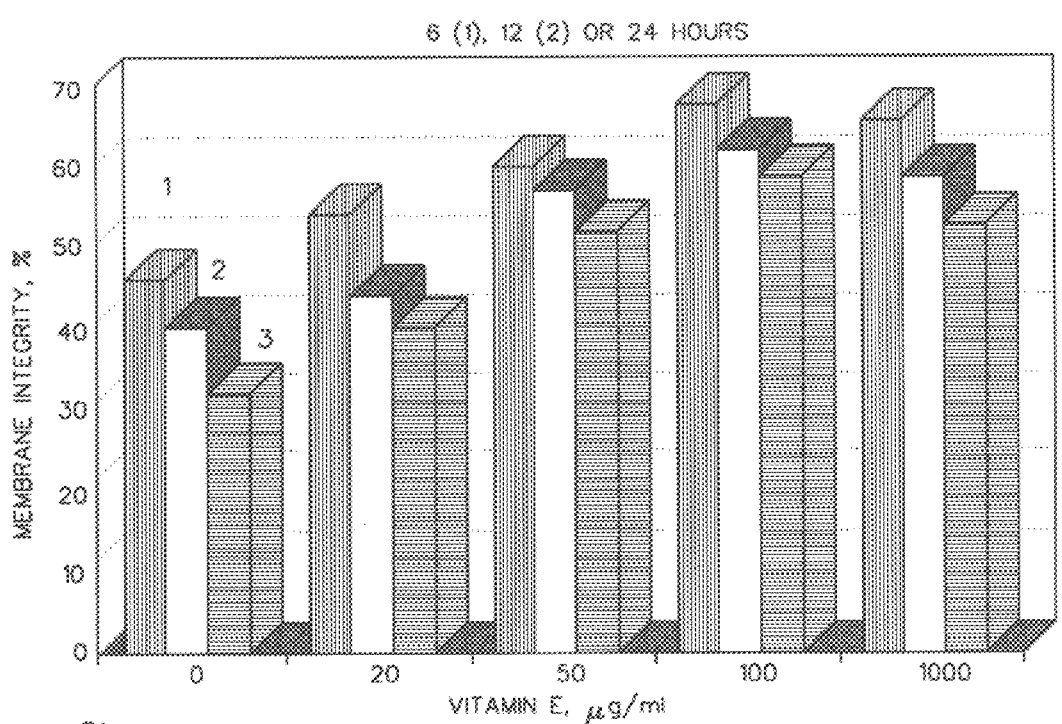
FIG. 7 is a graph depicting sperm viability vs vitamin E added after storage during 6 (1), 12(2) or 24 (3) hours at 37° C.
Figure 8:
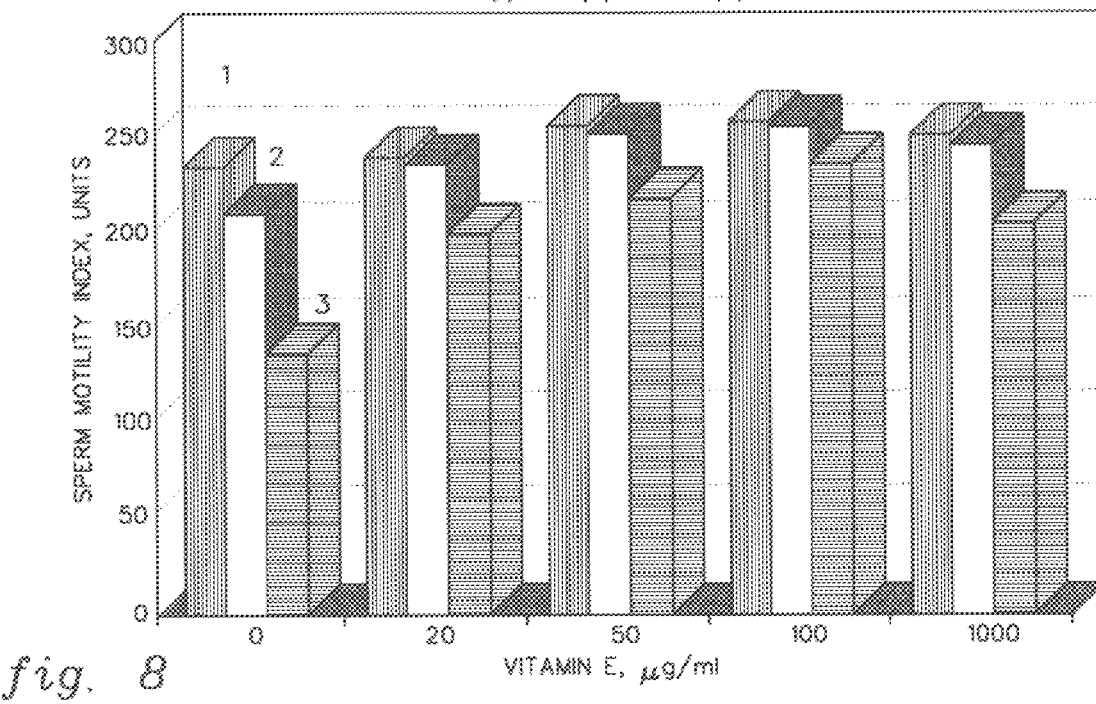
FIG. 8 is a graph depicting sperm motility vs vitamin E added after storage during 24 (1), 48(2) or 72 (3)hours at 4° C.
Figure 9:
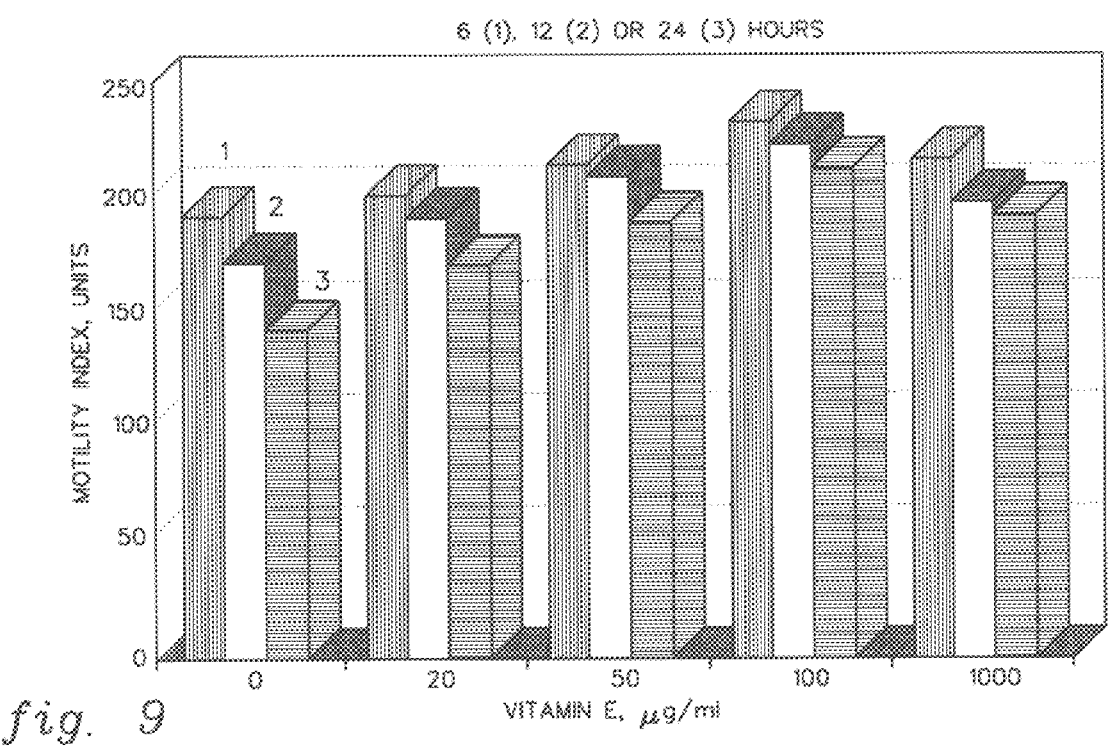
FIG. 9 is a graph depicting sperm motility vs vitamin E added after storage during 6 (1), 12(2) or 24 (3) hours at 37° C.
Figure 10:
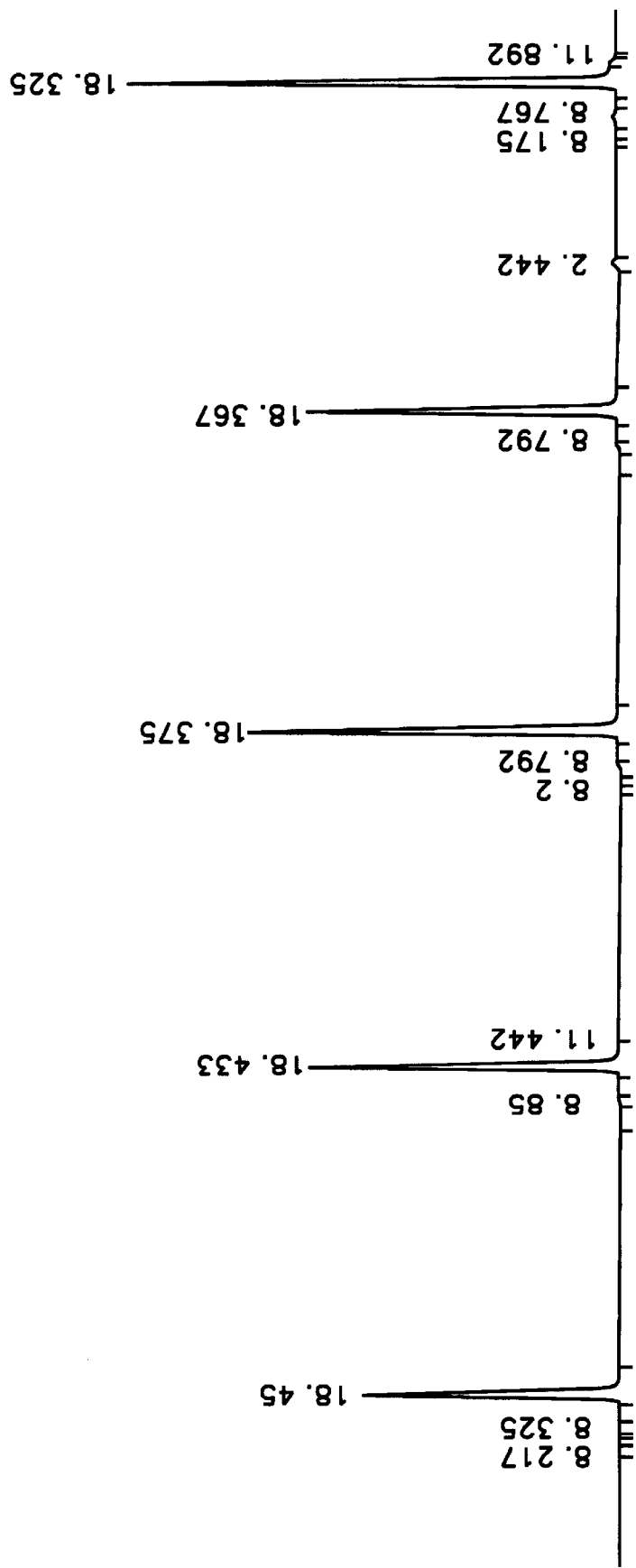
FIG. 10 is a chart from five HPLC runs (four replicates and a standard solution) showing -tocopherol distribution in the seminal plasma enriched by viatmin E at 400 µg/ml.
Figure 11:
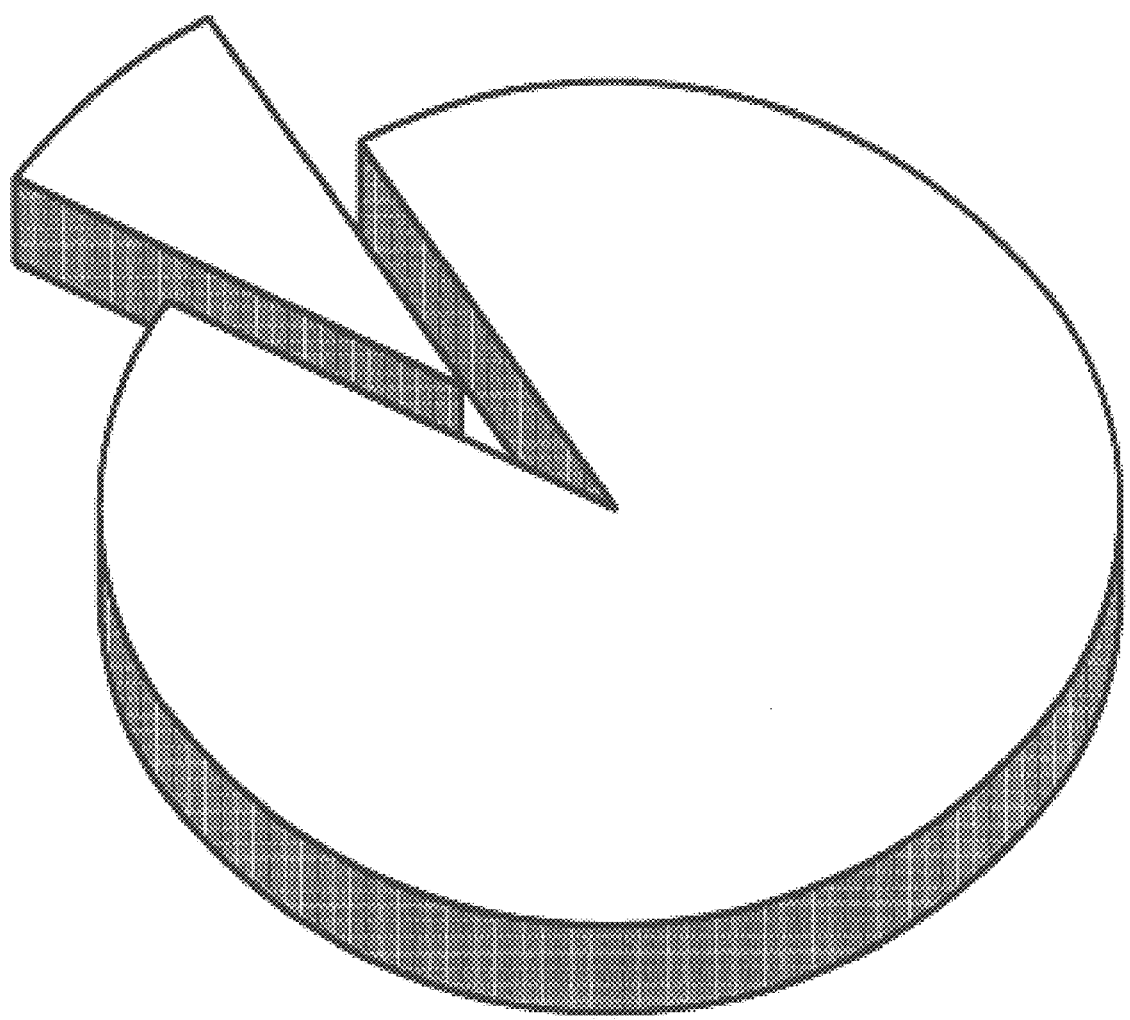
FIG. 11 is a pie chart depicting the proportion of vitamin E incorporated into the spermatozoa.
Figure 12:
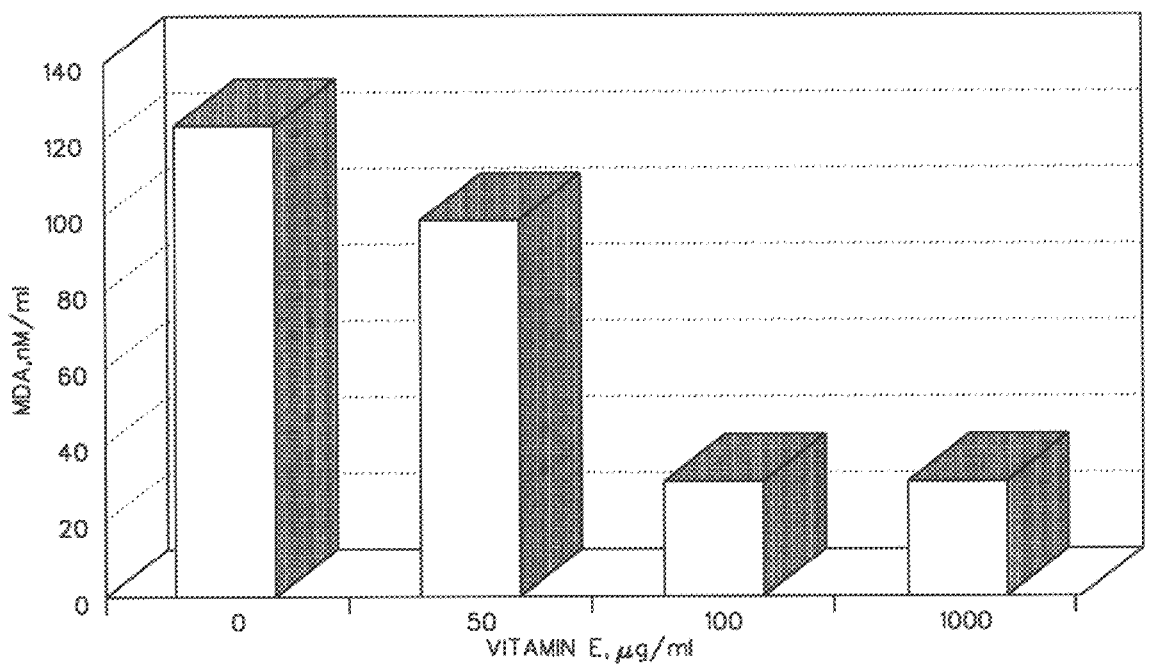
FIG. 12 is a graph depicting lipid peroxidation in sperm vs vitamin E added..

The main problem of spermatozoa storage is membrane damage as a result of lipid peroxidation. Under such conditions membrane permeability is dramatically increased and fertilisation capacity reduced. As can be seen from FIGS. 6 and 7 the inclusion of the diluent significantly increased sperm membrane integrity after storage at both 4° C. and 37° C. The effect of all these parameter changes under normal conditions is to diminish considerably sperm motility after storage. A pronounced protective effect of the diluent on spermatozoa motility following storage at 4° C. and 37° C. was observed (see FIGS. 8 and 9). That vitamin E was distributed uniformly throughout the semen was verified by appropriate determination of α-tocopherol from different parts of diluted semen (see FIG. 10). It was significant that after incubation of the spermatozoa, some 8% of the α-tocopherol had become incorporated into the membranes (See FIG. 11) and it was not possible to remove it during 3–5 consecutive washings with pure diluent. Confirmation of the protective effect of the diluent against lipid peroxidation sperm was further obtained by incubation of the spermatozoa in the presence of $Fe^{2++}$ at 37° C. The results obtained (see FIG. 12) indicate that malondialdehyde accumulation was less than one third that of the control spermatozoa.

Discussion

There is an overwhelming preponderance of linoleic (18:2 n-6) in proprietary feeds of domestic farm animals. Other fatty acids of the n-6 series and those of the n-3 series are notable by their virtual absence. That such a predominance of linoleic acid may not always be wholly beneficial to the well-being and health of the animal through effects upon tissue fatty acid composition and aspects of metabolism is now being asked. With such a high-profile presence of long chain polyunsaturated fatty acids of the n-3 series in mammalian sperm lipids, it is suggested that the alteration of the current fatty acid profile of animal proprietary feeds towards increasing levels of acids of the n-3 series may be highly relevant to the ontogeny of the characteristic fatty acid profiles and subsequent function of the sperm. Similarly, in the avian the high profile presence of C20 and C22 polyunsaturates of the n-6 series would also suggest the need to attempt their improved availability. Presently reported are the results from experiments designed to evaluate the deliberate enhancement of the diets of the cockerel and bull with fatty acids of the n-3 series and n-6 upon the lipid/fatty acid profile of the spermatozoa and associated changes to parameters of spermatozoa function and fertility.

It is clear from the analyses that initial lipid/fatty acid compositions of the spermatozoa of the 2 species conformed to that which has been previously reported. Thus, whereas in both species the lipids of the spermatozoa displayed extremely high levels of polyunsaturates, in the bull there was predominance of 22:6 (n-3) and in the cockerel 22:4 (n-6). The apparent substitution of 22:4 (n-6) for 22:6 (n-3) in the cockerel can be suggested to be the reaction to an almost complete domination in the diet of linoeic acid (18:2, n-6) and thereby determining that 22:4 (n-6) as opposed to 22:6 (n-3) be the long chain polyunsaturate for spermatozoa inclusion.

The inclusion of the n-3 fatty acids in the diet was to increase significantly their levels within the spermatozoa and to have extensive beneficial effects on parameters of spermatozoa function and therefore male fertility in the species. Although in the case of the cockerel these was a marked difference in the levels attainable within the spermatozoa of the long chain n-3 polyunsaturates, nevertheless effects on spermatozoa parameters were very positive. 22:6 (n-3) is an extensively available fatty acid. It is clear from the present results that deliberate enhancement of this acid within the diet of the cockerel and bull and also long chain polyunsaturates of the n-6 series in the cockerel presents a simple and effective means of promoting a range of parameters that lead to increased spermatozoa quality, output and viability at ejaculation. In the case of the cockerel, the result was to lead to a significant increase in output of the fertile eggs from the hen, a most important feature to commercial production. Similarly in the case of the bull, a dramatic decrease in "non return" rates of heifers was observed.

Intensive animal production systems require an efficient insemination service, both natural and artificial. This is clearly dependent not only upon maximising the initial fertility of fresh ejaculates but also its maintenance during storage. The need exists to extend the life of semen for a fresh delivery service and enhance the ability to maintain spermatozoa function during the following cryoscopic storage in all farm animal species.

The present data have clearly demonstrated the ability to promote the maintenance of spermatozoa viability and function following cryoscopic storage through the addition of α-tocopherol, in particular through a unique carrier medium. A very broad range of spermatozoa characteristics were able to be increased compared with spermatozoa maintained under standard cryoscopic AI conditions. Apart from measurements in vivo, the effect of the carrier/α-tocopherol medium was to prevent the significant reductions that arise as a result of storage in a range of biochemical and physiological features that are known to be intimately associated with spermatozoa viability and function. The data clearly demonstrates a means whereby a significant enhancement of male fertility can be obtained following sperm storage in the liquid state.

The present work therefore underlines 2 major vectors through which male fertility in mammalian and avian species may be significantly enhanced with appropriate and significant benefits to subsequent stock production:

(i) by the deliberate manipulation of the spectrum and level of long chain fatty acid combinations within the spermatozoa by appropriate dietary means.

(ii) by the addition to the ejaculate prior to cryoscopic and hypothermic storage of α-tocopherol through a unique carrier medium, including harvested seminal fluid lipids from donor animals.

It is clear that the invention is transferable across species to include the human.

TABLE 1

The major fatty acids (per cent by weight of total) in the diets.

| major fatty acids: | Cockerel | | | Bull | | |
| --- | --- | --- | --- | --- | --- | --- |
| | Diet 1 (soyabean oil) | Diet 2 (linseed oil) | Diet 3 (fish oil) | Diet 4 (evening primrose oil) | Diet 1 (soyabean oil) | Diet 2 (fish oil) |
| palmitic(16:0) | 12 | 10 | 22 | 10 | 15 | 20 |
| stearic(18:0) | 4 | 4 | 6 | 2 | 3 | 4 |
| oleic(18:1, n-9) | 23 | 21 | 19 | 13 | 17 | 16 |
| linoleic(18:2, n-6) | 50 | 30 | 20 | 62 | 52 | 32 |
| linoleic(18:3, n-3) | 6 | 34 | 3 | 2 | 6 | 4 |
| docosahexaenoic (22:6, n-3) | <1 | <1 | 1 | 5(18:3n-6) | <1 | 11 |

TABLE 2

The effect of linolenic acid (18:3, n-3) supplementation on semen characteristics of the cockerel.

| | Week 24 | | Week 40 | | Week 54 | |
| --- | --- | --- | --- | --- | --- | --- |
| | Control | Treated | Control | Treated | Control | Treated |
| Sperm conc. ($10^9$ cells/ml) | 4.7 ± 0.5 | 5.0 ± 0.6 | 7.7 ± 0.6 | 7.6 ± 0.6 | 5.1 ± 0.9 | 6.8 ± 0.7* |
| motility (1%) | 56.4 ± 4.1 | 56.5 ± 4.4 | 54.5 ± 3.8 | 62.5 ± 5.1 | 33.8 ± 3.9 | 53.9 ± 4.7** |
| fertility (%) | | | | | | |
| Week 1 | 68.3 ± 4.9 | 62.7 ± 9.1 | 82.8 ± 4.9 | 96.8 ± 3.2* | 74.4 ± 4.6 | 76.8 ± 3.8 |
| Week 2 | 45.0 ± 7.1 | 58.4 ± 10.8 | 61.7 ± 4.7 | 57.5 ± 7.3 | 47.9 ± 6.4 | 54.6 ± 8.4 |

Values are means ± standard error. Significance of difference between control and treated: * $p < 0.05$, **$p = < 0.01$

TABLE 3

The effect of linolenic acid (18:3 n-3) supplementation on the concentration and proportion of the major lipid and phospholipid classes (per cent by weight of total) in the spermatozoa of the cockerel.

| | Week 24 | | Week 40 | | Week 54 | |
| --- | --- | --- | --- | --- | --- | --- |
| | Control | Treated | Control | Treated | Control | Treated |
| Total lipid μg/109 cells | 261.2 ± 12.1 | 240.0 ± 27.6 | 274.4 ± 16.9 | 316.0 ± 44.0 | 364.4 ± 75.3 | 427.7 ± 84.1 |
| Lipid class (% w/w of total lipid) | | | | | | |
| PL | 60.1 ± 3 | 68.3 ± 4.4 | 69.2 ± 2.1 | 68.5 ± 1.6 | 57.7 ± 1.4 | 57.4 '5 3.4 |
| FC | 12.6 ± 1.4 | 12.1 ± 2.6 | 12.9 ± 0.6 | 17.8 ± 0.9 | 24.8 ± 1.8 | 23.8 ± 1.8 |
| FFA | 4.9 ± 1.6 | 5.9 ± 1.0 | 6.9 ± 1.2 | 5.3 ± 0.5 | 9.0 ± 1.8 | 4.9 ± 1.4 |
| TG | 9.3 ± 3.1 | 5.3 ± 2.8 | 3.8 ± 1.1 | 3.2 ± 2.1 | 3.1 ± 0.7 | 4.7 ± 1.3 |
| CE | 13.1 ± 3.6 | 8.4 ± 3.9 | 7.2 ± 1.2 | 5.2 ± 0.8 | 8.5 ± 0.6 | 9.2 ± 2.2 |
| Phospholipid class (% w/w of total phospholipid) | | | | | | |
| PC | 32.3 ± 1.5 | 33.4 ± 1.1 | 25.4 ± 1.6 | 26.6 ± 1.3 | 34.7 ± 1.2 | 3.24 ± 1.1 |
| PE | 33.1 ± 1.6 | 31.7 ± 1.2 | 33.8 ± 1.2 | 32.9 ± 0.8 | 31.1 ± 0.4 | 32.9 ± 0.9 |
| PS | 19.2 ± 2.1 | 18.9 ± 0.7 | 24.4 ± 0.7 | 22.3 ± 0.8 | 20.0 ± 0.8 | 21.6 ± 0.5 |
| Sph | 10.5 ± 1.1 | 11.9 ± 1.3 | 11.5 ± 0.4 | 12.9 ± 2.9 | 8.4 ± 0.5 | 9.4 ± 0.5 |
| CL | 4.9 ± 0.5 | 4.1 ± 0.5 | 4.8 ± 0.4 | 5.2 ± 0.8 | 4.9 ± 0.3 | 3.7 ± 0.2 |

TABLE 3-continued

The effect of linolenic acid (18:3 n-3) supplementation on the concentration and proportion of the major lipid and phospholipid classes (per cent by weight of total) in the spermatozoa of the cockerel.

| | Week 24 | | Week 40 | | Week 54 | |
|---|---|---|---|---|---|---|
| | Control | Treated | Control | Treated | Control | Treated |

Values are means ± standard error.
PL = phospholipid; FC = free cholesterol; FFA = free fatty acid; TG = triacylglycrol; CE = cholesterol ester
PC = phosphatidyl choline; PE = phosphatidyl ethanolamine; PS = phosphatidyl serine; Sph = sphingomyelin;
CL = cardialipin.

TABLE 4

The effect of linolenic acid (18:3, n-3) supplementation on the polyunsaturated fatty acid concentrations (per cent by weight of total fatty acids) within the phospholipid fraction of the spermatozoa of the cockerel.

| | Week 24 | | Week 40 | | Week 54 | |
|---|---|---|---|---|---|---|
| | Control | Treated | Control | Treated | Control | Treated |
| n-6 acids: | | | | | | |
| 18:2(n-6) | 2.7 ± 0.2 | 2.4 ± 0.1 | 3.4 ± 0.5 | 2.3 ± 0.1 | 4.7 ± 0.4 | 3.7 ± 0.3 |
| 20:4(n-6) | 12.5 ± 0.4 | 13.1 ± 0.4 | 11.7 ± 0.4 | 12.1 ± 0.5 | 11.9 ± 0.2 | 11.7 ± 0.2 |
| 22:4(n-6) | 22.8 ± 1.1 | 23.0 ± 0.8 | 22.9 ± 1.0 | 19.9 ± 0.8 | 21.7 ± 1.4 | 19.2 ± 0.6 |
| n-3 acids: | | | | | | |
| 18:3(n-3) | 0.8 ± 0.5 | 1.2 ± 0.7 | nd | 0.4 ± 0.03 | nd | nd |
| 22:5(n-3) | 1.0 ± 0.2 | 0.8 ± 0.2 | 1.0 ± 0.1 | 5.3 ± 0.9** | 0.8 ± 0.05 | 3.4 ± 0.1** |
| 22:6(n-3) | 2.2 ± 0.1 | 2.4 ± 0.1 | 2.5 ± 0.2 | 2.3 ± 0.1 | 1.9 ± 0.1 | 2.4 ± 0.1* |
| C20-22 n-6/n-3 | | | | | | |
| ratio | 10.5 ± 1.4 | 10.0 ± 1.8 | 10.9 ± 0.5 | 4.5 ± 0.6** | 14.5 ± 0.6 | 5.6 ± 0.2** |

Values are means ± standard error; nd = not detectable. Significance of difference between control and treated: *$p < 0.05$; **$p < 0.01$.

TABLE 5

The effect of docosahexaenoic acid (22:6 n-3) supplementation on the C20 and C22 polyunsaturated fatty acid concentrations (per cent by weight of total fatty acids) within the phospholipid fraction of the spermatozoa of the cockerel.

| | Week 24 | | Week 40 | | Week 58 | |
|---|---|---|---|---|---|---|
| | Control | Treated | Control | Treated | Control | Treated |
| 20:4(n-6) | 13.0 ± 0.1 | 8.9 ± 0.1*** | 11.4 ± 0.3 | 8.6 ± 0.2*** | 10.7 ± 0.2 | 8.3 ± 0.2*** |
| 22:4(n-6) | 19.5 ± 0.8 | 8.5 ± 0.4*** | 21.7 ± 0.2 | 15.0 ± 0.6*** | 18.2 ± 0.4 | 12.4 ± 0.5*** |
| 22:5(n-3) | nil | nil | nil | nil | 1.9 ± 0.01 | 3.1 ± 0.1*** |
| 22:6(n-3) | 4.7 ± 0.1 | 13.3 ± 0.5*** | 3.8 ± 1.1 | 10.1 ± 0.2*** | 5.1 ± 0.2 | 9.1 ± 0.3*** |
| C20-22 n-6/n-3 ratio | 8.9 | 1.3*** | 8.7 | 2.3** | 4.1 | 1.7** |

Values are means ± standard error.
nd = not detectable.
Significance of difference between control and treated: ***$p < 0.001$.

TABLE 6

The effect of docosahexaenoic acid (22:6 n-3) supplementation on the concentration of 22:6 (n-3) (percent by weight of total fatty acid) within the major phospholipid fractions of the spermatozoa of the cockerel.

| | Week 24 | | Week 40 | | Week 58 | |
|---|---|---|---|---|---|---|
| | C | T | C | T | C | T |
| PC | 1.7 ± 0.3 | 7.0 ± 0.3*** | 1.1 ± 0.3 | 5.2 ± 0.4*** | 2.6 ± 0.2 | 5.7 ± 2.7 |
| PE | 6.7 ± 0.7 | 22.6 ± 1.4*** | 6.1 ± 1.2 | 16.4 ± 1.0*** | 9.4 ± 0.2 | 14.9 ± 1.1** |
| PS | 6.1 ± 0.9 | 20.5 ± 2.0*** | 5.6 ± 0.4 | 17.5 ± 1.1*** | 7.1 ± 0.7 | 13.1 ± 0.7*** |
| Spl | 4.6 ± 2.6 | 16.4 ± 2.3* | 25.5 ± 3.6 | 11.2 ± 3.6* | 14.4 ± 2.2 | 17.7 ± 2.3 |

TABLE 6-continued

The effect of docosahexaenoic acid (22:6 n-3) supplementation on the concentration of 22:6 (n-3) (percent by weight of total fatty acid) within the major phospholipid fractions of the spermatozoa of the cockerel.

|  | Week 24 | | Week 40 | | Week 58 | |
| --- | --- | --- | --- | --- | --- | --- |
|  | C | T | C | T | C | T |
| CL | 9.2 ± 0.2 | 24.2 ± 0.7*** | 5.3 ± 0.8 | 14.0 ± 1.8** | 2.7 ± 0.3 | 14.3 ± 1.6** |

Values are means ± standard error.
Significance of difference between control and treated: $p < 0.01$; *$p < 0.001$.
PL = phospholipid; FC = free cholesterol; FFA = free fatty acid; TG = triacylglycerol; CD = cholesterol ester
PC = phosphatidyl choline; PE = phosphatidyl ethanolamine; PS = phosphatidyl serine; Sph = sphingomyelin; CL = cardialipin.

TABLE 7

The effect of docosahexaenoic acid (22:6 n-3) supplementation on the major cockerel's sperm parameters at 50 weeks of age. The results of the 2nd experiment.

| Diet | Control (maize oil) | DHA | DHA + Vit. E |
| --- | --- | --- | --- |
| Semen volume, ml | 0.25 | 0.45** | 0.40** |
| Spermatozoa concentration $10^9$/ml | 3.05 | 3.11 | 3.01 |
| Total number of spermatozoa, $10^9$/ejaculate | 0.763 | 1.400** | 1.204** |
| Fertilizing capacity of the fresh semen, % | 80.6 | 84.8* | 86.9** |
| Fertilizing capacity of stored 24 h at 4° C. semen % | 70.4 | 69.6 | 77.9** |
| Testes weight, g | 20.95 | 30.11** | 37.14** |
| Body weight, kg | 5.37 | 5.69 | 5.89 |

Values are means. Significance of differences between control and treated groups */-P < 0.05; **/-P,0.01

TABLE 8

The effect of GLA (18:3n-6) supplementation on the major cockerel's sperm parameters at 40 weeks of age.

| Sperm parameters | Control | GLA |
| --- | --- | --- |
| volume ml | 0.62 ± 0.04 | 0.66 ± 0.07 |
| concentration $10^9$/ml | 3.70 ± 0.20 | 2.74 ± 0.37 |
| total sperm $10^9$/ejaculate | 2.28 ± 0.19 | 1.84 ± 0.35 |
| motility % | 48.9 ± 3.11 | 54.0 ± 3.70 |
| fertility 1st week[2] | 92.8 ± 2.58 | 90.3 ± 2.15 |
| fertility 2nd week[3] | 58.1 ± 5.46 | 74.9 ± 5.18 |
| fertility 3rd week[4] | 13.9 ± 3.32 | 18.9 ± 5.18 |

[2]fertility of the 1st week after AI, [3]fertility of the 2nd week after AI, [4]fertility of the 3rd week after AI.

TABLE 9

The effect of docosahexaenoic acid (22:6, n-3) supplementation on semen characteristics of the bull.

|  | Sperm conc. ($10^9$ cells/ml) | Standard Motility (%) | Standard PPM (%) | Acrosomal integrity (%) |
| --- | --- | --- | --- | --- |
| Freisian/Holstein: | | | | |
| pre-treatment | 0.6 ± 0.1 | 3.3 ± 0.2 | 21.7 ± 4.4 | 70.0 ± 1.2 |
| post-treatment | 0.9 ± 0.1* | 4.0 ± 0.1* | 36.0 ± 0.6* | 90.0 ± 2.0*** |
| Belgian Blue: | | | | |
| pre-treatment | 1.27 | 3.4 | 25 | 68 |
| post-treatment | 2.82 | 4.0 | 36 | 80 |

Values are mean ± standard error. Significance of difference between pre and post-treatment: *$p < 0.05$; **$p < 0.01$.

TABLE 10

Fresh semen in vitro characteristics of the Belgian Blue.

|  | Citrate test | | Standard drop | |
| --- | --- | --- | --- | --- |
| treatment | motility | PPM | motility | PPM |
| A | 3 | 26 | 4 | 39 |
| B | 4* | 38* | 4 | 40* |
| C | 3.5 | 35* | 4 | 38 |
| D | 3 | 30* | 4 | 37 |
| E | 3 | 27 | 4 | 35 |
| F | 3 | 15 | 3.5 | 34 |
| G | 3 | 18 | 3.5 | 36 |

*Parameters greater than those of the control

TABLE 11

Fresh semen in vitro characteristics of the Holstein/Fresian.

|  | Citrate test | | Standard drop | |
| --- | --- | --- | --- | --- |
| treatment | motility | PPM | motility | PPM |
| A | 3.5 | 36 | 3.5 | 35 |
| B | 4* | 37* | 4* | 38* |
| C | 4* | 35 | 4* | 36* |
| D | 3 | 36 | 3.5 | 36* |
| E | 3.5 | 35 | 3.5 | 34 |
| F | 4* | 38* | 3.5 | 35 |
| G | 3.5 | 36 | 4* | 37* |

*Parameters greater than those of the control.

TABLE 12

Frozen semen in vitro characteristics of the Belgian Blue following storage at −196° C..

| treat-ment | Citrate test | | Standard drop | | Acrosomal integrity % | | |
|---|---|---|---|---|---|---|---|
| | motility | PPM | motility | PPM | abnormal | non intact | intact |
| A | 3 | 22 | 3 | 10 | 31 | 28 | 72 |
| B | 3 | 20 | 2.5 | 13* | 37 | 29 | 71 |
| C | 3 | 15 | 2.5 | 13* | 33 | 29 | 71 |
| D | 3.5 | 15 | 2 | 7 | 30 | 28 | 72 |
| E | 2 | 17 | 2.5 | 12* | 37 | 39 | 61 |
| F | 2.5 | 20 | 3 | 8 | 14* | 34 | 55 |
| G | 2 | 25* | 3 | 10 | 14* | 55 | 44 |

*Parameters greater than those of the control.

TABLE 13

Frozen semen in vitro characteristics of the Holstein/Fresian following storage at −196° C.

| treat-ment | Citrate test | | Standard drop | | Acrosomal integrity % | | |
|---|---|---|---|---|---|---|---|
| | motility | PPM | motility | PPM | abnormal | non intact | intact |
| A | 3.5 | 34 | 3 | 23 | 16 | 18 | 82 |
| B | 4* | 35* | 3.5* | 29* | 13* | 14* | 86* |
| C | 3.5 | 30 | 3.5* | 22 | 14* | 17* | 83* |
| D | 35 | 30 | 3 | 18 | 10* | 18 | 82 |
| E | 3 | 25 | 3 | 20 | 16 | 36 | 64 |
| F | 3 | 10 | 2.5 | 15 | 10* | 28 | 72 |
| G | 3.5 | 31 | 3 | 14 | 13* | 18 | 82 |

*Parameters greater than those of the control.

TABLE 14

| in vivo inseminations performed on synchronised heifers. | | |
|---|---|---|
| Treatment | A | B |
| Trial 1: | | |
| % heifers pregnant | 56 | 64 |
| Trial 2: | | |
| % heifers pregnant | 31 | 55 |

What is claimed is:

1. A method of enhancing male fertility and sperm function comprising adding to the semen of an animal in vitro an (n-3) polyunsaturated fatty acid.

2. A method as claimed in claim 1 comprising further adding to the semen of an animal an antioxidant.

3. A method as claimed in claim 2 wherein the antioxidant is selected from vitamins, plant extracts and carotenoids.

4. A method as claimed in claim 1 or 2 wherein the polyunsaturated fatty acid, or the polyunsaturated fatty acid and antioxidant, is added to the sperm or to the fluid surrounding the sperm.

5. A method as claimed in claim 1 or 2 wherein the polyunsaturated fatty acid, or the polyunsaturated fatty acid and antioxidant, is added to the semen in a carrier.

6. A method as claimed in claim 5 wherein the carrier is sperm-free seminal fluid.

7. A method as claimed in claim 6 wherein said seminal fluid is produced from the semen of another animal.

8. A method as claimed in claim 5 wherein the semen with the carrier is then placed in cryoscopic storage.

9. A method as claimed in claim 5 wherein the semen with the carrier is used for artificial insemination.

* * * * *